(12) United States Patent
Eriksson et al.

(10) Patent No.: US 10,772,890 B2
(45) Date of Patent: Sep. 15, 2020

(54) USE OF MYELOPEROXIDASE (MPO) INHIBITORS OR PHARMACEUTICALLY ACCEPTABLE SALTS THEREOF TO TREAT MULTIPLE SYSTEM ATROPHY (MSA) 938

(71) Applicant: ASTRAZENECA AB, Södertälje (SE)

(72) Inventors: Hakan Eriksson, Södertälje (SE); Werner Poewe, Innsbruck (AT)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 16/117,020

(22) Filed: Aug. 30, 2018

(65) Prior Publication Data

US 2019/0099423 A1  Apr. 4, 2019

Related U.S. Application Data

(63) Continuation of application No. 15/863,166, filed on Jan. 5, 2018, now abandoned, which is a continuation of application No. 15/608,453, filed on May 30, 2017, now abandoned, which is a continuation of application No. 14/075,790, filed on Nov. 8, 2013, now abandoned, which is a continuation of application No. 13/666,504, filed on Nov. 1, 2012, now abandoned, which is a continuation of application No. 13/033,220, filed on Feb. 23, 2011, now abandoned, which is a continuation of application No. 12/195,527, filed on Aug. 21, 2008, now abandoned.

(60) Provisional application No. 60/957,523, filed on Aug. 23, 2007, provisional application No. 60/957,525, filed on Aug. 23, 2007.

(51) Int. Cl.
*A61K 31/519* (2006.01)
*A61K 31/522* (2006.01)

(52) U.S. Cl.
CPC .......... *A61K 31/519* (2013.01); *A61K 31/522* (2013.01)

(58) Field of Classification Search
None
See application file for complete search history.

(56) References Cited

U.S. PATENT DOCUMENTS

| | | | | |
|---|---|---|---|---|
| 7,829,707 B2* | 11/2010 | Bogevig | ............. | C07D 487/04 544/280 |
| 8,859,568 B2* | 10/2014 | Bogevig | ............. | C07D 487/04 514/265.1 |
| 9,580,429 B2* | 2/2017 | Bogevig | ............. | C07D 487/04 |

FOREIGN PATENT DOCUMENTS

| | | | | |
|---|---|---|---|---|
| WO | WO-2006062465 A1 * | 6/2006 | ........... | C07D 487/04 |
| WO | WO-2007142577 A1 * | 12/2007 | ........... | C07D 487/04 |

OTHER PUBLICATIONS

Stefanova et al. "Myeloperoxidase Inhibition Ameliorates Multiple System Atrophy-Like Degeneration in a Transgenic Mouse Model". Neurotox Res. 2012; 21:393-404. (Year: 2012).*
Reagan-Shaw et al. "Dose Translation from Animal to Human Studies Revisited". FASEB J. 2007; 22:659-661. (Year: 2007).*

* cited by examiner

Primary Examiner — Leslie A. Royds Draper

(57) ABSTRACT

The present invention relates to the use of myeloperoxidase inhibitors (MPO) inhibitors for the treatment of multiple system atrophy. The present invention also relates to the use of MPO inhibitors for the treatment of Huntington's disease. The present invention also relates to the use of MPO inhibitors for neuroprotection.

2 Claims, 8 Drawing Sheets

SNc

Dopaminergic terminals in striatum

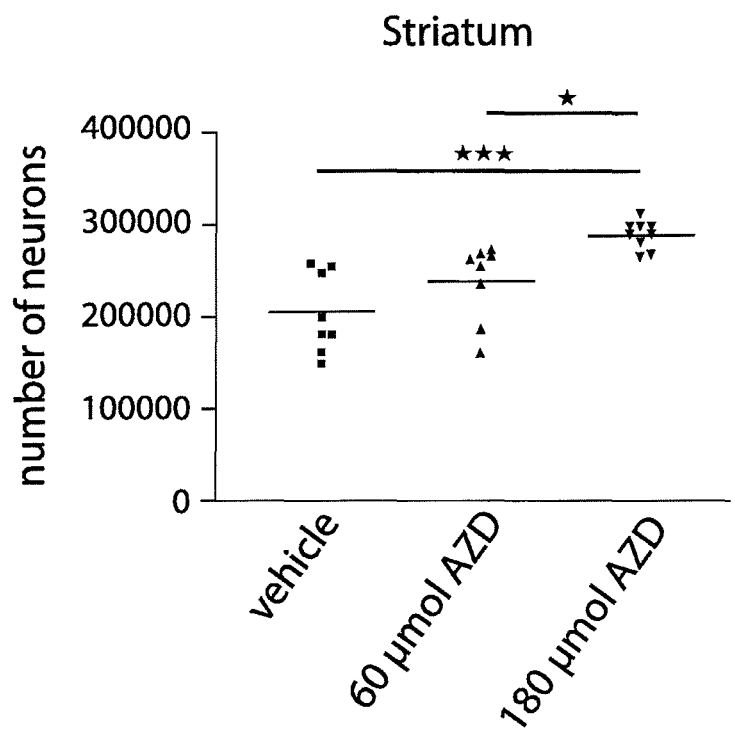

USE OF MYELOPEROXIDASE (MPO) INHIBITORS OR PHARMACEUTICALLY ACCEPTABLE SALTS THEREOF TO TREAT MULTIPLE SYSTEM ATROPHY (MSA) 938

CROSS-REFERENCE TO RELATED APPLICATIONS

This application is a continuation of U.S. application Ser. No. 15/863,166, filed on Jan. 5, 2018 (now abandoned); which is a continuation of U.S. application Ser. No. 15/608,453, filed on May 30, 2017 (now abandoned); is a continuation of U.S. application Ser. No. 14/075,790, filed on Nov. 1, 2012 (now abandoned); which is a continuation of U.S. application Ser. No. 13/666,504, filed on Nov. 8, 2013 (now abandoned); which is a continuation of U.S. application Ser. No. 13/033,220, filed on Feb. 23, 2011 (now abandoned); which is a continuation of U.S. application Ser. No. 12/195,527, filed on Aug. 21, 2008 (now abandoned); which claims the benefit of and priority to U.S. Provisional Application No. 60/957,525, filed Aug. 23, 2007, and U.S. Provisional Application No. 60/957,523, filed Aug. 23, 2007. The specifications of each of the foregoing applications are hereby incorporated by reference in their entirety.

The present invention relates to the use of Myeloperoxidase (MPO) inhibitors or pharmaceutically acceptable salts thereof for the treatment of multiple system atrophy (MSA). The present invention further relates to the use of Myeloperoxidase (MPO) inhibitors or pharmaceutically acceptable salts thereof for the treatment of Huntington's disease (HD). The present invention also relates to the use of Myeloperoxidase (MPO) inhibitors or pharmaceutically acceptable salts thereof for neuroprotection.

Myeloperoxidase (MPO) is a heme-containing enzyme found predominantly in polymorphonuclear leukocytes (PMNs). MPO is one member of a diverse protein family of mammalian peroxidases that also includes eosinophil peroxidase, thyroid peroxidase, salivary peroxidase, lactoperoxidase, prostaglandin H synthase, and others. The mature enzyme is a dimer of identical halves. Each half molecule contains a covalently bound heme that exhibits unusual spectral properties responsible for the characteristic green colour of MPO. Cleavage of the disulphide bridge linking the two halves of MPO yields the hemi-enzyme that exhibits spectral and catalytic properties indistinguishable from those of the intact enzyme. The enzyme uses hydrogen peroxide to oxidize chloride to hypochlorous acid. Other halides and pseudohalides (like thiocyanate) are also physiological substrates to MPO.

PMNs are of particular importance for combating infections. These cells contain MPO, with well-documented microbicidal action. PMNs act non-specifically by phagocytosis to engulf microorganisms, incorporate them into vacuoles, termed phagosomes, which fuse with granules containing myeloperoxidase to form phagolysosomes. In phagolysosomes the enzymatic activity of the myeloperoxidase leads to the formation of hypochlorous acid, a potent bactericidal compound. Hypochlorous acid is oxidizing in itself, and reacts most avidly with thiols and thioethers, but also converts amines into chloramines, and chlorinates aromatic amino acids. Macrophages are large phagocytic cells, which, like PMNs, are capable of phagocytosing microorganisms. Macrophages can generate hydrogen peroxide and upon activation also produce myeloperoxidase. MPO and hydrogen peroxide can also be released to the outside of the cells where the reaction with chloride can induce damage to adjacent tissue.

Linkage of myeloperoxidase activity to disease has been implicated in neurological diseases with a neuroinflammatory response including multiple sclerosis, Alzheimer's disease and Parkinson's disease.

MPO positive cells are immensely present in the circulation and in tissue undergoing inflammation. More specifically MPO containing macrophages, microglia, astrocytes and/or neurons have been documented in the CNS during disease; multiple sclerosis (Nagra R M, et al. Journal of Neuroimmunology 1997; 78(1-2):97-107; Marik C, et al. Brain. 2007; 130: 2800-15; Gray E, et al. Brain Pathology. 2008; 18: 86-95), Parkinson's disease (Choi D-K. et al. J. Neurosci. 2005; 25(28):6594-600) and Alzheimer's disease (Reynolds W F, et al. Experimental Neurology. 1999; 155: 31-41; Green P S. et al. Journal of Neurochemistry. 2004; 90(3):724-33). It is supposed that some aspects of a chronic ongoing inflammation result in an overwhelming destruction where agents from MPO reactions have an important role.

The enzyme is released both extracellularly as well as into phagolysosomes in the neutrophils (Hampton M B, Kettle A J, Winterbourn C C. Blood 1998; 92(9):3007-17). A prerequisite for the MPO activity is the presence of hydrogen peroxide, generated by NADPH oxidase and a subsequent superoxide dismutation. The oxidized enzyme is capable to use a plethora of different substrates of which chloride is most recognized. From this reaction the strong non-radical oxidant—hypochlorous acid (HOCl)—is formed. HOCl oxidizes sulphur containing amino acids like cysteine and methionine very efficiently (Peskin A V, Winterbourn C C. Free Radical Biology and Medicine 2001; 30(5):572-9). It also forms chloramines with amino groups, both in proteins and other biomolecules (Peskin A V. et al. Free Radical Biology and Medicine 2004; 37(10):1622-30). It chlorinates phenols (like tyrosine) (Hazen S L. et al. Mass Free Radical Biology and Medicine 1997; 23(6):909-16) and unsaturated bonds in lipids (Albert C J. et al. J. Biol. Chem. 2001; 276(26):23733-41), oxidizes iron centers (Rosen H, Klebanoff S J. Journal of Biological Chemistry 1982; 257(22): 13731-354) and crosslinks proteins (Fu X, Mueller D M, Heinecke J W. Biochemistry 2002; 41(4):1293-301). Various compounds that are MPO inhibitors are disclosed in WO 01/85146, J. Heterocyclic Chemistry, 1992, 29, 343-354, J. Chem. Soc., 1962, 1863, WO03/089430 and WO2006/062465.

Multiple System Atrophy (MSA)

Multiple system atrophy (MSA) is a neurodegenerative disorder presenting with autonomic failure and with motor impairment resulting from L-dopa-unresponsive parkinsonism, cerebellar ataxia and pyramidal signs. Histologically, there is neuron loss in the striatum, substantia nigra pars compacta, cerebellum, pons, inferior olives and intermediolateral column of the spinal cord. Glial pathology includes astrogliosis, microglial activation and α-synuclein containing oligodendroglial cytoplasmic inclusions. The pronounced neuroinflammation with activated microglia contribution as well as cytoplasmic inclusion bodies, containing aggregated and oxidatively modified proteins, makes it intriguing to consider a significant contribution of MPO activity in the progressive neurodegeneration characterizing the MSA pathology.

Support for MPO inhibition in an MSA-like pathology can be generated through the use of preclinical disease models for MSA, like transgenic mice with oligodendroglial overexpression of human α-synuclein with or without a toxin addition like 3-nitropropionic acid.

Huntington's Disease (HD)

Huntington's disease (HD) is a hereditary progressive neurodegenerative disorder characterized clinically by motor and psychiatric disturbances and pathologically by neuronal loss and gliosis (reactive astrocytosis) particularly in the striatum and cerebral cortex. HD is a neurodegenerative disorder caused by expansion of a CAG repeat in the HD gene, coding for polyglutamine in the huntingtin protein. Explanations to the pathological mechanisms include oxidative stress, impaired energy metabolism, and abnormal protein-protein interactions. Such mechanisms are possible to link to MPO activity, which might be manifested through its observed overexpression in pathological HD tissue (Choi D-K. et al. J. Neurosci. 2005; 25(28):6594-600).

Support for MPO inhibition in an HD-like pathology can be generated through the use of preclinical disease models for HD. Such models might be mice or rats treated with mitochondrial toxins like 3-nitropropionic acid or malonate (Matthews R T. et al J. Neurosci. 1998; 18:156-63). Useful models might also be transgenic mice expressing mutants of the huntingtin protein with or without a toxin addition like 3-nitropropionic acid (Bogdanov M B. et al. J. Neurochem. 1998; 71:2642-44).

There is a large unmet need for medications that can be used for the treatment of Huntington's disease, for the treatment of multiple system atrophy and/or for neuroprotection.

FIG. 4C is a graph depicting the number of neurons in the striatum of MSA mice treated with AZD (compound I) and vehicle.

Figure 1:
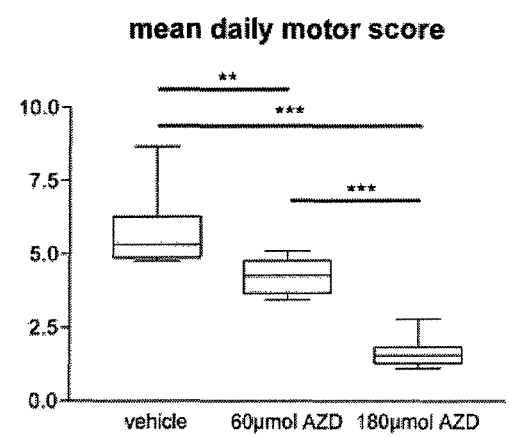
FIG. 1 is a graph depicting the mean daily motor score of MSA mice treated with AZD (compound I) and vehicle.

It has been found that MPO inhibitors can be used for the treatment of multiple system atrophy (MSA).

Consequently, the present invention is directed to the use of a MPO inhibitor for the manufacture of a medicament for the treatment of multiple system atrophy (MSA).

The wording "multiple system atrophy" as used herein, means a fatal progressive neurodegenerative disorder. It is defined as a sporadic alpha-synucleinopathy with dysautonomia and Parkinsonian and/or cerebellar motor impairment.

It has also been found that MPO inhibitors or pharmaceutically acceptable salts thereof can be used for the treatment of Huntington's disease (HD).

Consequently, the present invention is also directed to the use of a MPO inhibitor or a pharmaceutically acceptable salt thereof for the manufacture of a medicament for the treatment of Huntington's disease.

The wording "Huntington's disease" as used herein, is intended to define a hereditary progressive neurodegenerative disorder characterized clinically by motor and psychiatric disturbances and pathologically by neuronal loss and gliosis (reactive astrocytosis) particularly in the striatum and cerebral cortex.

Further, the present invention is also related to the use of MPO inhibitors or a pharmaceutically acceptable salt thereof for neuroprotection. Consequently, the present invention is directed to the use of a MPO inhibitor for the manufacture of a medicament for neuroprotection.

The term "neuroprotection" as used herein is defined as prevention of nerve cell loss and/or sparing of nerve cell fibers.

The term "treating" as used herein, refers to reversing, alleviating, delaying or inhibiting the progress of, or preventing the disorder or condition to which such term applies, or one or more symptoms of such disorder or condition. The term "treatment", as used herein, refers to the act of "treating" as defined herein.

Examples of compounds that can be used as MPO-inhibitors are the following:

1) A compound of formula (I)

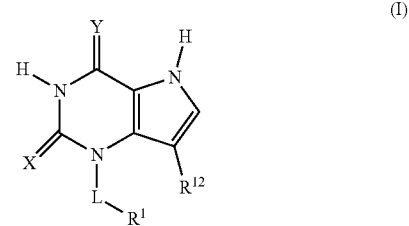

wherein:

At least one of X and Y represents S, and the other represents O or S;

L represents a direct bond or $C_{1-7}$alkylene, wherein said $C_{1-7}$alkylene optionally incorporating a heteroatom selected from O, S $(O)_n$ and $NR^6$, and said $C_{1-7}$alkylene optionally incorporating one or two carbon-carbon double bonds, and said $C_{1-7}$alkylene is optionally substituted by one or more substituents selected independently from OH, halogen, CN and $NR^4R^5$, $C_{1-6}$alkyl and $C_{1-6}$alkoxy, said $C_{1-6}$alkoxy optionally incorporating a carbonyl adjacent to the oxygen;

n represents an integer 0, 1 or 2;

$R^1$ is hydrogen, or $R^1$ is a saturated or partially unsaturated 3 to 7 membered ring optionally incorporating one or two heteroatoms selected independently from O, N and S, and optionally incorporating a carbonyl group, wherein said ring is optionally substituted by one or more substituents independently selected from halogen, $SO_2R^9$, $SO_2NR^9R^{10}$, OH, $C_{1-7}$alkyl, $C_{1-7}$alkoxy, CN, $CONR^2R^3$, $NR^2COR^3$ and $COR^3$, wherein said $C_{1-7}$alkoxy being optionally further substituted by $C_{1-6}$alkoxy and optionally incorporating a carbonyl adjacent to the oxygen, and said $C_{1-7}$alkyl being optionally further substituted by hydroxy or $C_{1-6}$alkoxy and said $C_{1-7}$alkyl or $C_{1-6}$alkoxy optionally incorporating a carbonyl adjacent to the oxygen or at any position in the $C_{1-7}$alkyl; or $R^1$ is an aromatic ring system selected from phenyl, biphenyl, naphthyl or a monocyclic or bicyclic heteroaromatic ring structure containing 1 to 3 heteroatoms independently selected from O, N and S, said aromatic ring system being optionally substituted by one or more substituents independently selected from halogen, $SO_2R^9$, $SO_2NR^9R^{10}$, OH, $C_{1-7}$alkyl, $C_{1-7}$alkoxy, CN, $CONR^2R^3$, $NR^2COR^3$ and $COR^3$; said $C_{1-7}$alkoxy being optionally further substituted by $C_{1-6}$alkoxy and said $C_{1-6}$alkoxy optionally incorporating a carbonyl adjacent to the oxygen, and said $C_{1-7}$alkyl being optionally further substituted by hydroxy or $C_{1-6}$alkoxy and said $C_{1-7}$alkyl or $C_{1-6}$alkoxy optionally incorporating a carbonyl adjacent to the oxygen or at any position in the alkyl;

$R^{12}$ represents hydrogen or halogen or a carbon optionally substituted with one to three halogen atoms;

at each occurrence, $R^2$, $R^3$, $R^4$, $R^5$, $R^6$, $R^9$ and $R^{10}$ independently represent hydrogen, $C_{1-6}$alkyl or $C_{1-6}$alkoxy said alkoxy optionally incorporating a carbonyl adjacent to the oxygen, said $C_{1-6}$alkyl being optionally further substituted by halogen, $C_{1-6}$alkoxy, CHO, $C_{2-6}$alkanoyl, OH, $CONR^7R^8$ and $NR^7COR^8$;

or the groups $NR^2R^3$, $NR^4R^5$ and $NR^9R^{10}$ each independently represent a 5 to 7 membered saturated azacyclic ring optionally incorporating one additional heteroatom selected from O, S and $NR^{11}$, said azacyclic ring being optionally further substituted by halogen, $C_{1-6}$alkoxy, CHO, $C_{2-6}$alkanoyl, OH, $CONR^7R^8$ and $NR^7COR^8$;

at each occurrence $R^7$, $R^8$ and $R^{11}$ independently represent hydrogen or $C_{1-6}$alkyl, or the group $NR^7R^8$ represents a 5- to 7-membered saturated azacyclic ring optionally incorporating one additional heteroatom selected from O, S and $NR^{11}$;

or pharmaceutically acceptable salts, solvates of solvates of salts thereof. These compounds are described in WO 2006/062465.

2) A compound selected from the group consisting of:
1-butyl-2-thioxo-1,2,3,5-tetrahydro-pyrrolo[3,2-d]pyrimidin-4-one;
1-isobutyl-2-thioxo-1,2,3,5-tetrahydro-pyrrolo[3,2-d]pyrimidin-4-one;
1-(pyridin-2-ylmethyl)-2-thioxo-1,2,3,5-tetrahydro-pyrrolo[3,2-d]pyrimidin-4-one;
1-(2-fluoro-benzyl)-2-thioxo-1,2,3,5-tetrahydro-pyrrolo[3,2-d]pyrimidin-4-one;
1-[2-(2-methoxyethoxy)-3-propoxybenzyl]-2-thioxo-1,2,3,5-tetrahydro-pyrrolo[3,2-d]pyrimidin-4-one;
1-(6-ethoxy-pyridin-2-ylmethyl)-2-thioxo-1,2,3,5-tetrahydro-pyrrolo[3,2-d]pyrimidin-4-one;
1-piperidin-3-ylmethyl-2-thioxo-1,2,3,5-tetrahydro-pyrrolo[3,2-d]pyrimidin-4-one;
1-butyl-4-thioxo-1,3,4,5-tetrahydro-2H-pyrrolo[3,2-d]pyrimidin-2-one;
1-(2-isopropoxyethyl)-2-thioxo-1,2,3,5-tetrahydro-pyrrolo[3,2-d]pyrimidin-4-one;
1-(2-methoxy-2-methylpropyl)-2-thioxo-1,2,3,5-tetrahydro-pyrrolo[3,2-d]pyrimidin-4-one;
1-(2-ethoxy-2-methylpropyl)-2-thioxo-1,2,3,5-tetrahydro-pyrrolo[3,2-d]pyrimidin-4-one;
1-(piperidin-4-ylmethyl)-2-thioxo-1,2,3,5-tetrahydro-pyrrolo[3,2-d]pyrimidin-4-one;
1-[(1-methylpiperidin-3-yl)methyl]-2-thioxo-1,2,3,5-tetrahydro-pyrrolo[3,2-d]pyrimidin-4-one;
1-[2-hydroxy-2-(4-methoxyphenyl)ethyl]-2-thioxo-1,2,3,5-tetrahydro-pyrrolo[3,2-d]pyrimidin-4-one;
1-(2-methoxybenzyl)-2-thioxo-1,2,3,5-tetrahydro-pyrrolo[3,2-d]pyrimidin-4-one;
1-(3-methoxybenzyl)-2-thioxo-1,2,3,5-tetrahydro-pyrrolo[3,2-d]pyrimidin-4-one;
1-(2,4-dimethoxybenzyl)-2-thioxo-1,2,3,5-tetrahydro-pyrrolo[3,2-d]pyrimidin-4-one;
1-[(3-chloropyridin-2-yl)methyl]-2-thioxo-1,2,3,5-tetrahydro-pyrrolo[3,2-d]pyrimidin-4-one;
1-{[3-(2-ethoxyethoxy)pyridin-2-yl]methyl}-2-thioxo-1,2,3,5-tetrahydro-pyrrolo[3,2-d]pyrimidin-4-one;
1-[(6-oxo-1,6-dihydropyridin-2-yl)methyl]-2-thioxo-1,2,3,5-tetrahydro-pyrrolo[3,2-d]pyrimidin-4-one;
1-(1H-indol-3-ylmethyl)-2-thioxo-1,2,3,5-tetrahydro-pyrrolo[3,2-d]pyrimidin-4-one;
1-(1H-benzimidazol-2-ylmethyl)-2-thioxo-1,2,3,5-tetrahydro-pyrrolo[3,2-d]pyrimidin-4-one;
1-[(5-chloro-1H-indol-2-yl)methyl]-2-thioxo-1,2,3,5-tetrahydro-pyrrolo[3,2-d]pyrimidin-4-one;
1-[(5-fluoro-1H-indol-2-yl)methyl]-2-thioxo-1,2,3,5-tetrahydro-pyrrolo[3,2-d]pyrimidin-4-one;
1-(1H-indol-6-ylmethyl)-2-thioxo-1,2,3,5-tetrahydro-pyrrolo[3,2-d]pyrimidin-4-one;
1-(1H-indol-5-ylmethyl)-2-thioxo-1,2,3,5-tetrahydro-pyrrolo[3,2-d]pyrimidin-4-one;
1-[(5-fluoro-1H-indol-3-yl)methyl]-2-thioxo-1,2,3,5-tetrahydro-pyrrolo[3,2-d]pyrimidin-4-one;
1-(1H-imidazol-5-ylmethyl)-2-thioxo-1,2,3,5-tetrahydro-pyrrolo[3,2-d]pyrimidin-4-one;
1-(1H-imidazol-2-ylmethyl)-2-thioxo-1,2,3,5-tetrahydro-pyrrolo[3,2-d]pyrimidin-4-one;
1-[(5-chloro-1H-benzimidazol-2-yl)methyl]-2-thioxo-1,2,3,5-tetrahydro-pyrrolo[3,2-d]pyrimidin-4-one;
1-[(4,5-dimethyl-1H-benzimidazol-2-yl)methyl]-2-thioxo-1,2,3,5-tetrahydro-pyrrolo[3,2-d]pyrimidin-4-one;
7-bromo-1-isobutyl-2-thioxo-1,2,3,5-tetrahydro-pyrrolo[3,2-d]pyrimidin-4-one; and
1-(3-chlorophenyl)-2-thioxo-1,2,3,5-tetrahydro-pyrrolo[3,2-d]pyrimidin-4-one;

or pharmaceutically acceptable salts thereof, solvate or solvate of a salt thereof. These compounds are described in WO 2006/062465.

3) A compound of formula (IIa) or (IIb)

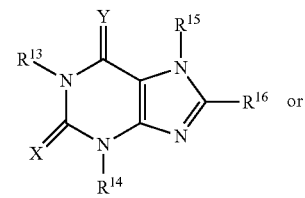

(IIa)

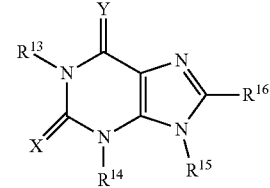

(IIb)

wherein:
one of X and Y represents S, and the other represents O or S;
$R^{13}$ represents hydrogen or $C_{1-6}$alkyl;

$R^{14}$ represents hydrogen or $C_{1-6}$alkyl; said $C_{1-6}$alkyl group being optionally substituted by:
  i) a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, $C_{1-6}$alkoxy and $C_{1-6}$alkyl; said $C_{1-6}$alkyl being optionally further substituted by hydroxy or $C_{1-6}$alkoxy; or
  ii) $C_{1-6}$alkoxy; or
  iii) an aromatic ring selected from phenyl, furyl or thienyl; said aromatic ring being optionally further substituted by halogen, $C_{1-6}$alkyl or $C_{1-6}$alkoxy;
$R^{15}$ and $R^{16}$ independently represent hydrogen or $C_{1-6}$alkyl;
or a pharmaceutically acceptable salt, solvate or solvate of a salt thereof. These compounds are described in WO 2003/089430.

According to one aspect of the present invention said MPO inhibitor is selected from a compound of formula (IIa) or (IIb)

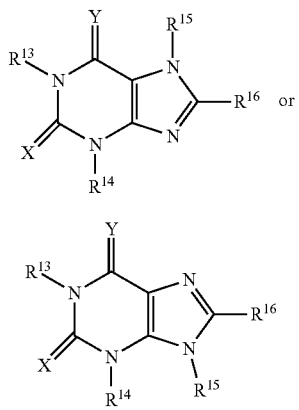

wherein:
X represents S, and Y represents O;
$R^{13}$ represents hydrogen or $C_{1-6}$alkyl;
$R^{14}$ represents $C_{1-6}$alkyl substituted by a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, $C_{1-6}$alkoxy and $C_{1-6}$alkyl; said alkyl being optionally further substituted by hydroxy or $C_{1-6}$alkoxy;
$R^{15}$ and $R^{16}$ independently represent hydrogen or $C_{1-6}$alkyl;
or pharmaceutically acceptable salts, solvates or solvates of a salt thereof. These compounds are described in WO 2003/089430.

4) A compound selected from the group consisting of:
1,3-diisobutyl-8-methyl-6-thioxanthine;
1,3-dibutyl-8-methyl-6-thioxanthine;
3-isobutyl-1,8-dimethyl-6-thioxanthine;
3-(2-methylbutyl)-6-thioxanthine;
3-isobutyl-8-methyl-6-thioxanthine;
3-isobutyl-2-thioxanthine;
3-isobutyl-2,6-dithioxanthine;
3-isobutyl-8-methyl-2-thioxanthine;
3-isobutyl-7-methyl-2-thioxanthine;
3-cyclohexylmethyl-2-thioxanthine;
3-(3-methoxypropyl)-2-thioxanthine;
3-cyclopropylmethyl-2-thioxanthine;
3-isobutyl-1-methyl-2-thioxanthine;
3-(2-tetrahydrofuryl-methyl)-2-thioxanthine;
3-(2-methoxy-ethyl)-2-thioxanthine;
3-(3-(1-morpholinyl)-propyl)-2-thioxanthine;
3-(2-furyl-methyl)-2-thioxanthine;
3-(4-methoxybenzyl)-2-thioxanthine;
3-(4-fluorobenzyl)-2-thioxanthine;
3-phenethyl-2-thioxanthine;
(+)-3-(2-tetrahydrofuryl-methyl)-2-thioxanthine;
(−)-3-(2-tetrahydrofuryl-methyl)-2-thioxanthine; and
3-n-butyl-2-thioxanthine;
or a pharmaceutically acceptable salt, solvate or solvate of a salt thereof. These compounds are described in WO 2003/089430.

The (−)-enantiomer of 3-(2-tetrahydrofuryl-methyl)-2-thioxanthine represents 3-(2R-tetrahydrofuryl-methyl)-2-thioxanthine and the (+)-enantiomer of 3-(2-tetrahydrofuryl-methyl)-2-thioxanthine represents 3-(2S-tetrahydrofuryl-methyl)-2-thioxanthine.

5) A compound of formula of Formula (III)

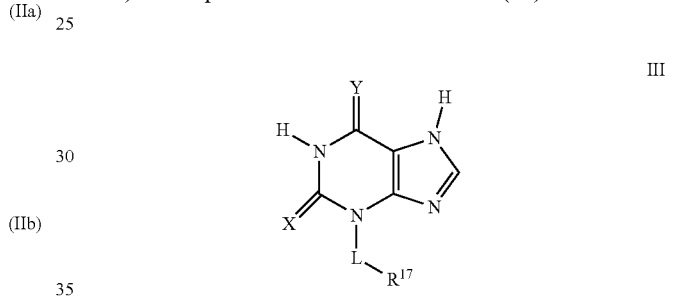

wherein
at least one of X and Y represents S, and the other represents O or S;
L represents $(R^{18})_p$-Q-R$(CR^{19}R^{20})_r$; wherein $(R^{18})_p$ and $(CR^{19}R^{20})_r$ each optionally contain one or two double or triple bonds;
wherein Q is O, S(O)$_n$, NR$^{21}$, NR$^{21}$C(O), C(O)NR$^{21}$, or a bond;
wherein R$^{18}$ is selected from $C_{1-6}$alkyl or $C_{1-6}$alkoxy, said $C_{1-6}$alkyl or said $C_{1-6}$alkoxy is optionally substituted with OH, halogen, CF$_3$, CHF$_2$, CFH$_2$, CN, NR$^{22}$R$^{23}$, phenoxy or aryl;
and wherein said phenoxy is optionally substituted with $C_{1-6}$alkyl, halogen or $C_{1-6}$alkoxy;
and wherein said phenoxy optionally incorporates a carbonyl adjacent to the oxygen and wherein said $C_{1-6}$alkoxy optionally incorporates a carbonyl adjacent to the oxygen;
wherein R$^{19}$ and R$^{20}$ are independently selected from hydrogen, OH, halogen, CF$_3$, CHF$_2$, CFH$_2$, CN, NR$^{22}$R$^{23}$, C1 to 6 alkyl, phenoxy and $C_{1-6}$alkoxy; wherein said phenoxy or $C_{1-6}$alkoxy optionally incorporates a carbonyl adjacent to the oxygen; and wherein said phenoxy is optionally substituted with $C_{1-6}$alkyl, halogen or $C_{1-6}$alkoxy;
wherein p represents an integer 0, 1, 2, 3 or 4 and r represents an integer 0, 1, 2, 3 or 4; and
wherein 1≤p+r≤7;
R$^{17}$ represents a mono- or bicyclic heteroaromatic ring system containing one or more heteroatoms selected from N, O and S; wherein said mono- or bicyclic heteroaromatic ring system is optionally fused with one or two 5- or 6-membered saturated or partially saturated ring(s) containing one or more atoms selected from C, N, O and S, wherein said mono- or bicyclic heteroaromatic ring system alone or when fused with one or two 5- or 6-membered saturated or partially saturated ring(s) is optionally substituted with one or more substituents independently selected from halogen, $CHF_2$, $CH_2F$, $CF_3$, $SO_{(n)}R^{24}$, $SO_{(n)}NR^{24}R^{25}$, $(CH_2)_nR^{26}$, $NR^{22}R^{23}$, OH, C1 to 7 alkyl, $C_{1-7}$alkoxy, phenoxy, aryl, CN, $C(O)NR^{27}R^{26}$, $NR^2C(O)R^{26}$, or a 5- or 6-membered saturated or partially saturated ring containing one or more atoms selected from C, N, O or S, and a mono- or bicyclic heteroaromatic ring system containing one or more heteroatoms selected from N, S or O;

and wherein said $C_{1-7}$alkoxy is optionally substituted with $C_{1-7}$alkoxy or aryl; and wherein said $C_{1-7}$alkoxy or said phenoxy is optionally incorporating a carbonyl adjacent to the oxygen; and wherein said $C_{1-7}$alkyl is optionally substituted with hydroxy or $C_{1-6}$alkoxy;

and wherein said $C_{1-7}$alkyl is optionally incorporating a carbonyl at any position in the C $C_{1-7}$alkyl; and wherein said phenoxy is optionally substituted with $C_{1-6}$alkyl, halogen or $C_{1-6}$alkoxy;

at each occurrence, $R^{27}$, $R^{26}$, $R^{22}$, $R^{23}$, $R^{21}$, $R^{24}$ and $R^{25}$ are independently selected from hydrogen, $C_{1-6}$alkyl, $C_{1-6}$alkoxy, aryl and phenoxy; said $C_{1-6}$alkoxy or phenoxy is optionally incorporating a carbonyl adjacent to the oxygen; and said $C_{1-6}$alkyl is optionally substituted with halogen, $C_{1-6}$alkoxy, CHO, $C_{2-6}$alkanoyl, OH, $C(O)NR^{28}R^{29}$ or $NR^{28}C(O)R^{29}$; and said aryl or said phenoxy is optionally substituted with $C_{1-6}$alkyl, halogen or $C_{1-6}$alkoxy;

or the groups $NR^{27}R^{26}$, $NR^{22}R^{23}$ and $NR^{24}R^{25}$ each independently represents a 5 to 7 membered saturated azacyclic ring optionally incorporating one additional heteroatom selected from O, S and $NR^{30}$, said ring being optionally further substituted with halogen, $C_{1-6}$alkoxy, CHO, $C_{2-6}$alkanoyl, OH, $C(O)NR^{28}R^{29}$ or $NR^{28}C(O)R^{29}$;

at each occurrence $R^{28}$, $R^{29}$ and $R^{30}$ independently represent hydrogen or $C_{1-6}$alkyl, or the group $NR^{28}R^{29}$ represents a 5 to 7 membered saturated azacyclic ring optionally incorporating one additional heteroatom selected from O, S and $NR^{30}$;

n represents an integer 0, 1 or 2;

with the proviso that for $R^{17}$ thienyl or furyl is excluded;

and with the proviso that when Q is O, $S(O)_n$, $NR^{21}$, $NR^{21}C(O)$ or $C(O)NR^{21}$, then p is greater or equal to 1;

or a pharmaceutically acceptable salt, solvate or solvate of a salt thereof. These compounds are described in PCT/SE2007/000349.

6) A compound selected from the group consisting of:
3-(pyridin-2-ylmethyl)-2-thioxo-1,2,3,7-tetrahydro-6H-purin-6-one;
3-(pyridin-3-ylmethyl)-2-thioxo-1,2,3,7-tetrahydro-6H-purin-6-one;
3-(pyridin-4-ylmethyl)-2-thioxo-1,2,3,7-tetrahydro-6H-purin-6-one;
3-{[3-ethoxy-4-(2-ethoxyethoxy)pyridin-2-yl]methyl}-2-thioxo-1,2,3,7-tetrahydro-6H-purin-6-one;
3-[(5-fluoro-1H-indol-2-yl)methyl]-2-thioxo-1,2,3,7-tetrahydro-6H-purin-6-one;
3-[(5-fluoro-1H-indol-2-yl)methyl]-2-thioxo-1,2,3,7-tetrahydro-6H-purin-6-one;
3-[(2-butyl-4-chloro-1H-imidazol-5-yl)methyl]-2-thioxo-1,2,3,7-tetrahydro-6H-purin-6-one;
3-(1H-benzimidazol-2-ylmethyl)-2-thioxo-1,2,3,7-tetrahydro-6H-purin-6-one;
3-[1-(1H-benzimidazol-2-yl)ethyl]-2-thioxo-1,2,3,7-tetrahydro-6H-purin-6-one;
3-[(5-chloro-1H-indol-3-yl)methyl]-2-thioxo-1,2,3,7-tetrahydro-6H-purin-6-one and
3-[(4-fluoro-1H-indol-3-yl)methyl]-2-thioxo-1,2,3,7-tetrahydro-6H-purin-6-one;
3-[2-(1H-Benzimidazol-2-yl)ethyl]-2-thioxo-1,2,3,7-tetrahydro-6H-purin-6-one;
3-(1H-Pyrazol-3-ylmethyl)-2-thioxo-1,2,3,7-tetrahydro-6H-purin-6-one;
3-[(5-Methylpyrazin-2-yl)methyl]-2-thioxo-1,2,3,7-tetrahydro-6H-purin-6-one;
3-[(3-Isopropylisoxazol-5-yl)methyl]-2-thioxo-1,2,3,7-tetrahydro-6H-purin-6-one;
3-[(4-Methyl-1,2,5-oxadiazol-3-yl)methyl]-2-thioxo-1,2,3,7-tetrahydro-6H-purin-6-one;
3-[(6-Butoxypyridin-2-yl)methyl]-2-thioxo-1,2,3,7-tetrahydro-6H-purin-6-one;
3-[(4-Butoxypyridin-2-yl)methyl]-2-thioxo-1,2,3,7-tetrahydro-6H-purin-6-one;
3-[(3-Butoxypyridin-2-yl)methyl]-2-thioxo-1,2,3,7-tetrahydro-6H-purin-6-one;
3-[2-(Pyridin-2-ylmethoxy)propyl]-2-thioxo-1,2,3,7-tetrahydro-6H-purin-6-one;
3-[(3,5-Dimethylisoxazol-4-yl)methyl]-2-thioxo-1,2,3,7-tetrahydro-6H-purin-6-one;
3-[(1-Methyl-1H-indol-2-yl)methyl]-2-thioxo-1,2,3,7-tetrahydro-6H-purin-6-one;
3-(2-Phenyl-2-pyridin-2-ylethyl)-2-thioxo-1,2,3,7-tetrahydro-6H-purin-6-one;
3-(Quinolin-4-ylmethyl)-2-thioxo-1,2,3,7-tetrahydro-6H-purin-6-one;
3-[(6-Phenoxypyridin-3-yl)methyl]-2-thioxo-1,2,3,7-tetrahydro-6H-purin-6-one;
3-{2-[(Quinolin-4-ylmethyl)amino]ethyl}-2-thioxo-1,2,3,7-tetrahydro-6H-purin-6-one;
3-(2-{[(1-Methyl-1H-indol-3-yl)methyl]amino}ethyl)-2-thioxo-1,2,3,7-tetrahydro-6H-purin-6-one;
3-{2-[Methyl(quinolin-4-ylmethyl)amino]ethyl}-2-thioxo-1,2,3,7-tetrahydro-6H-purin-6-one;
3-(2-Aminopropyl)-2-thioxo-1,2,3,7-tetrahydro-6H-purin-6-one trifluoroacetate;
3-{2-[(Pyridin-2-ylmethyl)amino]propyl}-2-thioxo-1,2,3,7-tetrahydro-6H-purin-6-one trifluoroacetate;
3-{2-[(Pyridin-3-ylmethyl)amino]propyl}-2-thioxo-1,2,3,7-tetrahydro-6H-purin-6-one;
3-{2-[(Pyridin-4-ylmethyl)amino]propyl}-2-thioxo-1,2,3,7-tetrahydro-6H-purin-6-one;
3-(2-{[(6-Chloropyridin-3-yl)methyl]amino}propyl)-2-thioxo-1,2,3,7-tetrahydro-6H-purin-6-one trifluoroacetate;
3-[2-({[6-(Trifluoromethyl)pyridin-3-yl]methyl}amino)propyl]-2-thioxo-1,2,3,7-tetrahydro-6H-purin-6-one trifluoroacetate;
3-(2-{[(4,6-Dichloropyrimidin-5-yl)methyl]amino}propyl)-2-thioxo-1,2,3,7-tetrahydro-6H-purin-6-one;
3-[2-({[2-(Dimethylamino)pyrimidin-5-yl]methyl}amino)propyl]-2-thioxo-1,2,3,7-tetrahydro-6H-purin-6-one;
3-{2-[(Quinolin-2-ylmethyl)amino]propyl}-2-thioxo-1,2,3,7-tetrahydro-6H-purin-6-one trifluoroacetate;
3-{2-[(Quinolin-3-ylmethyl)amino]propyl}-2-thioxo-1,2,3,7-tetrahydro-6H-purin-6-one;
3-(2-{[(1-tert-Butyl-3,5-dimethyl-1H-pyrazol-4-yl)methyl]amino}propyl)-2-thioxo-1,2,3,7-tetrahydro-6H-purin-6-one;
3-[2-({[1-(1,1-Dioxidotetrahydro-3-thienyl)-3,5-dimethyl-1H-pyrazol-4-yl]methyl}amino)propyl]-2-thioxo-1,2,3,7-tetrahydro-6H-purin-6-one;

3-{2-[(1H-Benzoimidazol-2-ylmethyl)amino]propyl}-2-thioxo-1,2,3,7-tetrahydro-6H-purin-6-one;
3-[2-({[1-(Phenylsulfonyl)-1H-pyrrol-2-yl]methyl}amino] propyl]-2-thioxo-1,2,3,7-tetrahydro-6H-purin-6-one trifluoroacetate;
3-{2-[({1-[(4-methylphenyl)sulfonyl]-1H-pyrrol-2-yl}methyl)amino]propyl}-2-thioxo-1,2,3,7-tetrahydro-6H-purin-6-one trifluoroacetate;
3-(2-{[(1-methyl-1H-pyrrol-2-yl)methyl]amino}propyl)-2-thioxo-1,2,3,7-tetrahydro-6H-purin-6-one;
3-[2-({[1-(4-sec-Butylphenyl)-1H-pyrrol-2-yl]methyl}amino)propyl]-2-thioxo-1,2,3,7-tetrahydro-6H-purin-6-one;
3-[2-({[1-(3-Methoxyphenyl)-1H-pyrrol-2-yl]methyl}amino)propyl]-2-thioxo-1,2,3,7-tetrahydro-6H-purin-6-one;
3-[2-({[2,5-Dimethyl-1-(1,3-thiazol-2-yl)-1H-pyrrol-3-yl]methyl}amino)propyl]-2-thioxo-1,2,3,7-tetrahydro-6H-purin-6-one;
3-[2-({[4-(3-Chlorobenzoyl)-1-methyl-1H-pyrrol-2-yl]methyl}amino)propyl]-2-thioxo-1,2,3,7-tetrahydro-6H-purin-6-one;
3-{2-[(1H-Imidazol-2-ylmethyl)amino]propyl}-2-thioxo-1,2,3,7-tetrahydro-6H-purin-6-one;
3-(2-{[(1-Methyl-1H-imidazol-2-yl)methyl]amino}propyl)-2-thioxo-1,2,3,7-tetrahydro-6H-purin-6-one;
3-(2-{[(4-Bromo-1-methyl-1H-imidazol-5-yl)methyl]amino}propyl)-2-thioxo-1,2,3,7-tetrahydro-6H-purin-6-one;
3-(2-{[(1-Methyl-1H-indol-3-yl)methyl]amino}propyl)-2-thioxo-1,2,3,7-tetrahydro-6H-purin-6-one;
2-Thioxo-3-{2-[(1H-1,2,3-triazol-5-ylmethyl)amino]propyl}-1,2,3,7-tetrahydro-6H-purin-6-one;
3-[2-({[1-(Benzyloxy)-1H-imidazol-2-yl]methyl}amino)propyl]-2-thioxo-1,2,3,7-tetrahydro-6H-purin-6-one;
3-(2-{[(6-Bromo-2-methylimidazo[1,2-a]pyridin-3-yl)methyl]amino}propyl}-2-thioxo-1,2,3,7-tetrahydro-6H-purin-6-one;
3-{2-[({1-[2-(2-Methoxyphenoxy)ethyl]-1H-pyrrol-2-yl}methyl)amino]propyl]-2-thioxo-1,2,3,7-tetrahydro-6H-purin-6-one;
N-[1-Methyl-2-(6-oxo-2-thioxo-1,2,6,7-tetrahydro-3H-purin-3-yl)ethyl]pyridine-2-carboxamide;
N-[1-Methyl-2-(6-oxo-2-thioxo-1,2,6,7-tetrahydro-3H-purin-3-yl)ethyl]nicotinamide;
N-[1-Methyl-2-(6-oxo-2-thioxo-1,2,6,7-tetrahydro-3H-purin-3-yl)-ethyl] isonicotinamide;
N-[1-methyl-2-(6-oxo-2-thioxo-1,2,6,7-tetrahydro-3H-purin-3-yl)ethyl]-1,8-naphthyridine-2-carboxamide;
N-[1-Methyl-2-(6-oxo-2-thioxo-1,2,6,7-tetrahydro-3H-purin-3-yl)ethyl]quinoline-2-carboxamide;
N-[1-Methyl-2-(6-oxo-2-thioxo-1,2,6,7-tetrahydro-3H-purin-3-yl)ethyl]pyrimidine-2-carboxamide; and
N-[1-Methyl-2-(6-oxo-2-thioxo-1,2,6,7-tetrahydro-3H-purin-3-yl)ethyl]-1H-imidazole-2-carboxamide trifluoroaceate;
or a pharmaceutically acceptable salt, solvate or solvate of a salt thereof. These compounds are described in PCT/SE2007/000349.

For use in medicine, pharmaceutically acceptable salts may be useful in the preparation of the compounds according to the present invention. Suitable pharmaceutically acceptable salts of the compounds described herein include acid addition salts which may, for example, be formed by mixing a solution of the compound according to the present invention with a solution of a pharmaceutically acceptable acid such as hydrochloric acid, sulfuric acid, methanesulphonic acid and fumaric acid. Furthermore, where the compounds carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "pharmaceutically acceptable salts" includes both pharmaceutically acceptable acid addition salts and pharmaceutically acceptable cationic salts. The expression "pharmaceutically acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine) and choline. The expression "pharmaceutically acceptable acid addition salts" is intended to define but is not limited to such salts as the hydrochloride, hydrobromide and sulfate.

The pharmaceutically acceptable cationic salts containing free carboxylic acids can be readily prepared by reacting the free acid form of with an appropriate base. Typical bases are sodium hydroxide, sodium methoxide and sodium ethoxide. The pharmaceutically acceptable acid addition salts containing free amine groups can be readily prepared by reacting the free base form with the appropriate acid.

The use of optical isomers of MPO inhibitors is also within the scope of the present invention. MPO inhibitors having an asymmetric carbon atom are chiral compounds, and depending on the presence of asymmetric atoms, the MPO inhibitors may exist in the form of mixtures of isomers, particularly racemates, or in the form of pure isomers such as specific enantiomers.

Pharmaceutical Formulations

The MPO inhibitors or pharmaceutically acceptable salts thereof described herein can be administered in a standard manner such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal or via a high-pressure technique.

For buccal administration, the MPO inhibitors or pharmaceutically acceptable salts thereof can be in the form of tablets or lozenges formulated in conventional manner. For example, tablets and capsules for oral administration can contain conventional excipients such as binding agents (e.g., syrup, acacia, gelatin, sorbitol, tragacanth, mucilage of starch or polyvinylpyrrolidone), fillers (e.g., lactose, sugar, microcrystalline cellulose, maize-starch, calcium phosphate or sorbitol), lubricants (e.g., magnesium stearate, stearic acid, talc, polyethylene glycol or silica), disintegrants (e.g., potato starch or sodium starch glycollate), or wetting agents (e.g., sodium lauryl sulfate). Tablets may be coated according to methods well known in the art. Such preparations can also be formulated as suppositories for rectal administration, e.g., containing conventional suppository bases, such as cocoa butter or other glycerides.

Compositions for inhalation comprising MPO inhibitors or pharmaceutically acceptable salts thereof can typically be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or non-aqueous vehicles, such as eye drops, creams, ointments, lotions, and pastes, or are in the form of a medicated plaster, patch, or membrane.

Additionally, MPO inhibitors or pharmaceutically acceptable salts thereof described herein can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

The MPO inhibitors or pharmaceutically acceptable salts thereof in accordance with the present invention also can be formulated as a depot preparation. Such long acting formulations can be administered by implantation (e.g., subcutaneously or intramuscularly) or by intramuscular injection. Accordingly, the compounds of the present invention can be formulated with suitable polymeric or hydrophobic materials (e.g., an emulsion in an acceptable oil), ion exchange resins, or as sparingly soluble derivatives (e.g., a sparingly soluble salt).

For oral administration a pharmaceutical composition comprising the MPO inhibitors or pharmaceutically acceptable salts thereof according to the present invention can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc may be used to form tablets. Solid compositions of a similar type are also employed as fillers in soft and hard-filled gelatin capsules; preferred materials in this connection also include lactose or milk sugar as well as high molecular weight polyethylene glycols.

Alternatively, the MPO inhibitors or pharmaceutically acceptable salts thereof described herein can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents, such as sorbitol syrup, synthetic and natural gums such as tragacanth, acacia, alginate, dextran, sodium carboxymethylcellulose, methylcellulose, polyvinyl-pyrrolidone or gelatin, glucose/sugar syrup, gelatin, hydroxyethylcellulose, hydroxypropylmethylcellulose, aluminum stearate gel, emulsifying agents, such as lecithin, sorbitan monooleate, or acacia; non-aqueous vehicles (which can include edible oils), such as almond oil, fractionated coconut oil, oily esters, propylene glycol, and ethyl alcohol; and preservatives, such as methyl or propyl p-hydroxybenzoate and sorbic acid. The liquid forms in which the compositions described herein may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

When aqueous suspensions and/or elixirs are desired for oral administration, the compounds described herein can be combined with various sweetening agents, flavoring agents, coloring agents, emulsifying agents and/or suspending agents, as well as such diluents as water, ethanol, propylene glycol, glycerin and various like combinations thereof. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The MPO inhibitors or pharmaceutically acceptable salts thereof described herein can also be administered in a controlled release formulation (definition) such as a slow release or a fast release formulation. Such controlled release formulations of the combinations described herein may be prepared using methods well known to those skilled in the art. The method of administration will be determined, by the attendant physician or other person skilled in the art after an evaluation of the patient's condition and requirements.

Thus, the effective dose of a MPO inhibitor or pharmaceutically acceptable salts thereof according to the present invention may vary, depending upon factors such as the condition of the patient, the severity of the symptoms of the disorder as well as the potency of the selected specific compound, the mode of administration, the age and weight of the patient, and the like. Determining a dose is within the skill of the ordinary artisan. The exact formulation, route of administration, and dosage can be chosen by the individual physician in view of the patient's condition. Dosage amount and interval can be adjusted individually to provide plasma levels of the active moiety, which are sufficient to maintain therapeutic effects.

Typically, the effective dose of MPO inhibitors or pharmaceutically acceptable salts thereof generally requires administering the compound in a range of from, and including, 1 to 1000 mg. According to one embodiment of the present invention, said range is from, and including, 2 to 800 mg or from, and including, 2 to 400 mg. In an alternative embodiment of the present invention the amount of MPO inhibitor is selected from about: 5, 10, 50, 100, 150, 200, 250, 300, 350, 400, 500, 550, 600, 700 and 800 mg.

Description of the Methods

The treatment of transgenic (tg) or wild type mice with 3NP constitutes also the most established models of HD3NP (Brouillet E. et al. Prog. Neurobiol. 1999; 59:427-68). It relies on subacute systemic injection of this mitochondrial-complex II toxin. In mice, this toxin creates HD-like striatal lesions and replicates the metabolic failure occurring in HD. During its extensive use a correlation (Fernagut P O. et al. Neuroscience. 2002; 114:1005-17) between the time-course and intensity of the motor disorder has been demonstrated, using a semiquantitative scale (rating bradykinesia, truncal dystonia, hindlimb dystonia and clasping and impaired postural control) and the severity of striatal damage (neuronal loss and astrocytic reaction). An impairment of sensorimotor integration has also been demonstrated using quantified tests known to be sensitive to striatonigral dysfunction: general activity, pole test and beam-traversing test. Consequently, several of the important behavioural and histopathological endpoints, of relevance for HD, are the same as in the used MSA model. Thus, the striatal pathology including neuronal loss and parts of the motor behaviour in the MSA model mentioned above also reflect the HD pathology.

A novel mouse model of MSA has been developed by inducing oxidative stress in transgenic mice with oligodendroglial α-synuclein expression (described herein). This model reproduces the cardinal neuropathological features of the disease including striatonigral degeneration (SND), olivopontocerebellar atrophy (OPCA), astrogliosis and microgliosis combined with oligodendroglial insoluble α-synuclein inclusions. Mitochondrial inhibition by 3NP in the presence of glial cytoplasmic inclusions in transgenic mice induces a selective neuronal cell death pattern typical for MSA in these animals (Stefanova N. et al. Am. J. Pathol. 2005; 166:869-76).

Thus, in the present invention, MPO inhibitors have been use to suppress MPO activity in an MSA mouse model consisting of an oligodendroglial α-SYN overexpression in transgenic mice exposed to mitochondrial inhibition by 3-nitropropionic acid (3NP). The effects were followed by application of established immunohistological and behavioral methods to evaluate the participation of MPO in the pathogenesis of MSA and the possible neuroprotective effects of in an MSA model.

Transgenic substantia nigra pars compacta (SNc) is undergoing early neuronal loss associated with the oligodendroglial α-synucleinopathy during the time window between two and four months of age. This early neuronal loss was correlated with microglial activation in the SNc. Suppression of microgliosis in the time period between 2 and 4 months of age was found to be neuroprotective for nigral neurons. The findings suggest that the combined transgenic and neurotoxic MSA mouse model should lend itself as a pre-clinical test for novel therapeutic candidates for MSA, both for early "minimal change" or late progressed "full-blown" MSA paradigms.

Microglial activation is a prominent finding in MSA brains. It was shown, in transgenic mice overexpressing human wild type a-synuclein under the control of the proteolipid protein (PLP) promoter, that such mice had intense microglial activation especially in the white matter, which is not the case in wild type C57Bl/6 mice (Stefanova N. et al. Am. J. Pathol. 2005; 166:869-76). Further, microglial activation is highly intensified following 3NP exposure and accompanied by MSA-like neuronal degeneration. The correlation of microglial activation with neuronal cell loss suggests that microglial factors might at least partially mediate neurodegeneration by releasing reactive oxygen species, nitrogen oxide (NO), cytokines, or chemokines.

Animals

A total of 30 (PLP)-α-synuclein transgenic mice were used. Animals were housed at 12/12 hours dark/light cycle with free access to food and water in the animal facility of the Innsbruck Medical University. All experiments were performed in accordance with the Austrian law and after permission for animal experiments of the Federal Ministry for Education, Science, and Culture of Austria.

Groups

Control group (n=10) MSA mice (tg+3NP), treated with vehicle (Cyclodextrin, prepared by AstraZeneca) p.o. (per oral administration)

Low dose group (n=10) MSA mice (tg+3NP) treated with 1-(2-Isopropoxyethyl)-2-thioxo-1,2,3,5-tetrahydro-pyrrolo[3,2-d]pyrimidin-4-one (Compound I; prepared by AstraZeneca), 2×6 μmol/kg p.o.

High dose group (n=10) MSA mice (tg+3NP) treated with Compound I (prepared by AstraZeneca), 2×180 μmol/kg, p.o.

1-(2-Isopropoxyethyl)-2-thioxo-1,2,3,5-tetrahydro-pyrrolo[3,2-d]pyrimidin-4-one (Compound I treatment) was started one week prior to the first 3NP intoxication and stopped three weeks after the first 3NP intoxication (see 3NP intoxication protocol below). Animals underwent behavioral tests during week 3-4 after the beginning of the experiment. On day 28 animals were perfused under deep thiopental anesthesia and the brains were collected for histopathological analysis of neuronal loss and gliosis.

3NP Intoxication

Mice were intoxicated chronically with 3NP with slowly increasing doses of toxin according to a previously used scheme (i.e. 4×10 mg/kg, 4×20 mg/kg, 4×40 mg/kg, 4×50 mg/kg intraperitoneal injections every 12th hour for a period of 8 days) to model MSA (Stefanova N. et al. Am. J. Pathol. 2005; 166:869-76)

Compound I Treatment

The drug and vehicle (0.1 mol/L meglumine with 20% w/v hydroxypropyl-β-cyclodextrin, pH 10.8) were stored at 4° C. Mice received the necessary dose of drug/vehicle (10 mL/kg) twice daily by oral gavage during the indicated period.

Behaviour

Behavioural tests were performed blindly to the treatment status according to validated procedures: clinical scale evaluation, pole test and stride length spontaneous locomotor activity test (Stefanova N. et al. Am. J. Pathol. 2005; 166:869-76)

Motor Clinical Scale Evaluation

A previously described rating scale for evaluation of hindlimb clasping, general locomotor activity, hindlimb dystonia, truncal dystonia and postural challenge response (0, normal; 1 slightly disturbed, and 2 markedly disabled). (Fernagut P O. et al. Neuroscience. 2002; 114:1005-17)

Open Field Activity

To test the locomotor activity of the mice the Flex Field Activity System (San Diego Instruments, CA, USA) was applied, which allows monitoring and real-time counting of horizontal and vertical locomotor activity by 544 photobeam channels. Mice was placed in the center of the open field (40.5×40.5×36.5 cm) and tested for a 15 min period always at the same time of the day (17.00 h). The tests were performed in a dark room that was completely isolated from external noises and light during the test period.

Stride Length

The stride length of the forelimbs and hindlimbs of the mice was measured after a habituation to the test for 3 days before its performance according to Fernagut et al. (Fernagut P O. et al. Neuroscience. 2002; 114:1005-17) with slight modification. The limbs of each animal were wetted with a non-toxic food colour and each mouse was let to run on a strip of paper (42 cm long, 4.5 cm wide) down a bright corridor towards a dark goal box. After three runs, the stride length of the hindlimbs on each side was measured, excluding the beginning (7 cm) and the end (7 cm) of the run. The mean stride length for each limb was determined.

Tissue Preparation

Animals were perfused under thiopental overdose with 4% paraformaldehyde (PFA) pH=7.4. Brains were quickly removed and stored for 24 hours in 4% PFA at 4° C. After cryoprotection in a 20% sucrose/0.1M PBS pH 7.4 solution, the brains were frozen and stored at −80° C. Serial sections (total of 7 series) were cut on cryostat (Leica) and collected for histological stainings (one series on slides) and immunohistochemistry (6 series free floating).

Nissl staining: Coronal sections throughout the whole brain were mounted on slides and processed for standard cresyl violet staining.

Immunocytochemistry was performed according to standard protocols (Stefanova N. et al. Am. J. Pathol. 2005; 166:869-76) on free floating sections (40 μm) to analyze neuronal and glial pathology in MSA mouse model. The following primary antibodies were used: anti-TH tyrosine hydroxylase (Sigma); anti-DARPP-32 (dopamine and cyclic adenosine 3',5'-monophosphate-regulated phosphoprotein 32); anti-GFAP (glial fibrillary acidic protein, Roche Diagnostics GmbH); anti-CD11b: (Serotec). Secondary antibodies were biotinylated anti-mouse or anti-rat IgG as appropriate. Shortly, after washing in phosphate buffered saline (PBS), sections were incubated in 0.3% $H_2O_2$, rinsed again and blocked for 1 hour in 10% normal goat serum in PBS with 0.3% Triton-X100 (PBS-T), followed by overnight incubation in the primary antibody at 4° C. After washing in PBS-T, slices were incubated for 1 hour in the secondary antibody, washed again and incubated for another hour in avidin-biotin complex (Elite Kit, Vector). Finally the reaction was visualized by 3,3'-diaminobenzidine.

Stereology was applied using a computer-assisted image analysis system (Nikon E-800 microscope, CCD video camera, Optronics MicroFire, Goleta, USA; Stereo Investigator Software, MicroBrightField Europe e.K., Magdeburg, Germany). Optical fractionator was used to count neurons in the striatum, substantia nigra pars compacta, pontine nuclei, and inferior olives. Purkinje cells were counted in a region outlined to include only the Purkinje cell layer as previously reported (German D C. et al. Neuroscience. 2001; 105:999-1005). All data were expressed as mean value±SEM. Glial activation in substantia nigra and striatum was measure by determining optical density in the target region by delineating its area in serial sections. For all statistical tests performed, a probability level of 5% ($p<0.05$) was considered significant.

Results

Effects of Compound I Treatment on Motor Behaviour of MSA Mice

Figure 2:
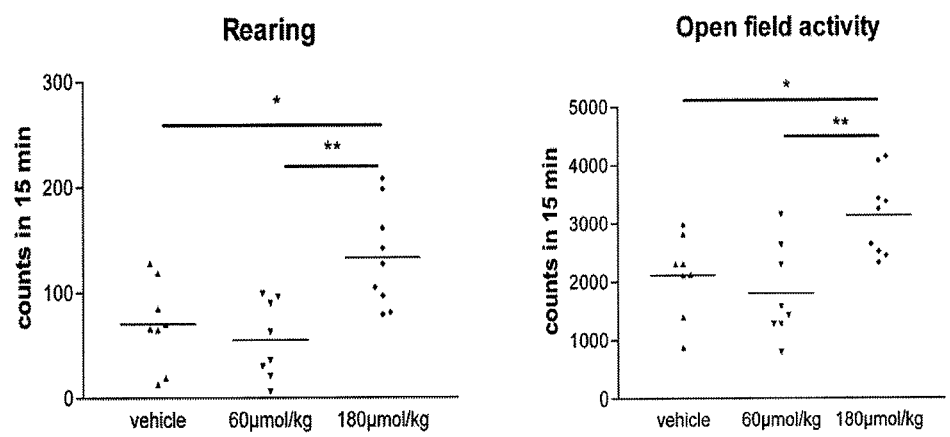
FIG. 2 is a graph depicting the rearing and open field activity of MSA mice treated with AZD (compound I) and vehicle.
Figure 3:
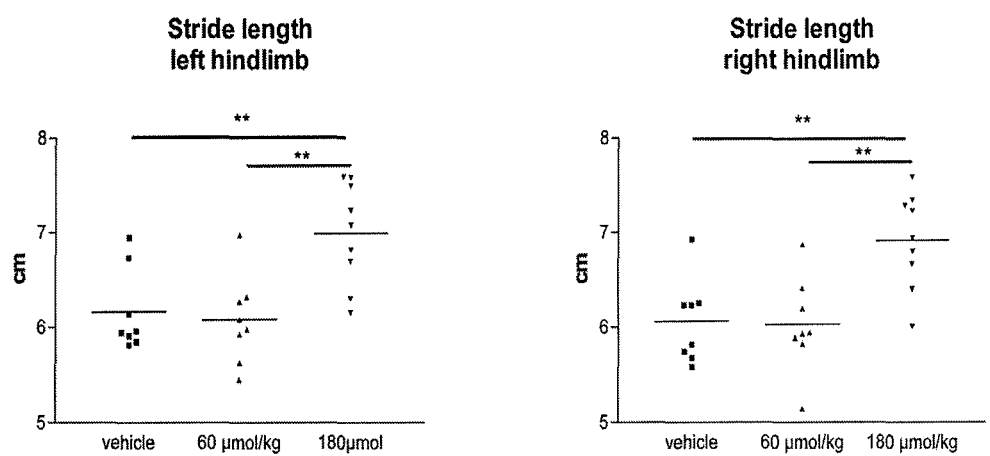
FIG. 3 is a graph depicting stride length of the left and right hindlimbs of MSA mice treated with AZD (compound I) and vehicle.

There was a significant improvement in the mean daily motor score in MSA mice treated with Compound I compared to vehicle treated mice (FIG. 1). There was also a significant improvement in flex field performance after treatment with high dose Compound I (180 µmol/kg). Both rearing and open field activity was affected (FIG. 2). Similarly, there was a significant improvement in stride length test performance after treatment with high dose Compound I (180 µmol/kg), both left and right hindlimbs were equally affected (FIG. 3).

Effects of Compound I Treatment on Neuropathology of MSA Mice

Figure 4A:
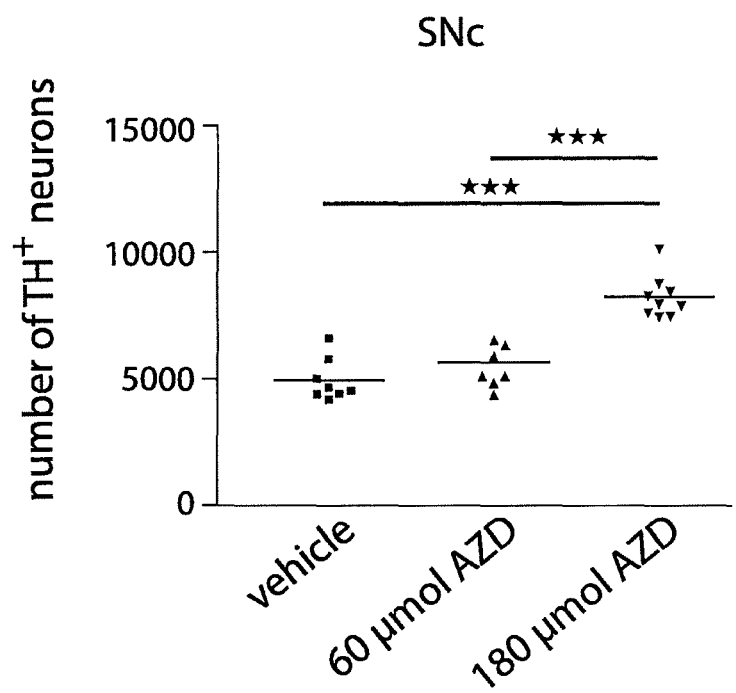
FIG. 4A is a graph depicting the number of TH immunopositive cells in the substantia nigra pars compacta (SNc) of MSA mice treated with AZD (compound I) and vehicle.
Figure 4B:
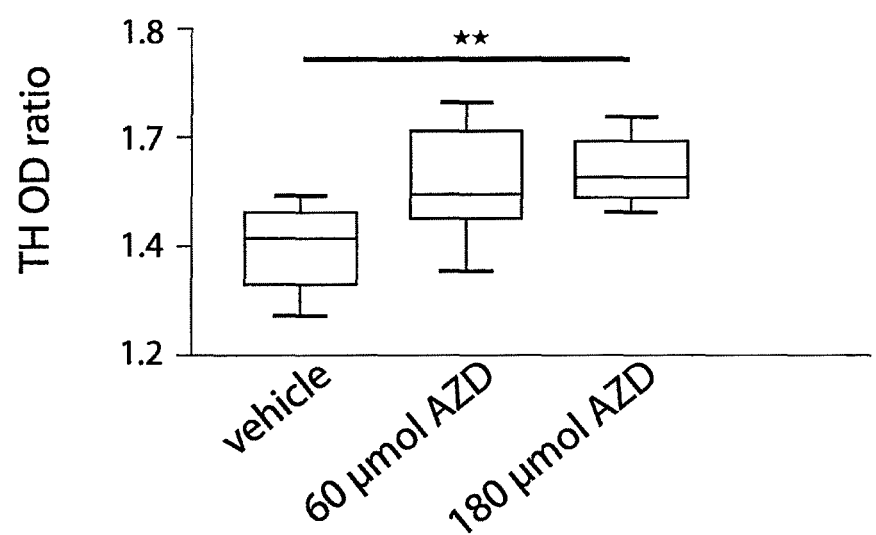
FIG. 4B is a graph depicting the dopaminergic terminals in striatum of MSA mice treated with AZD (compound I) and vehicle.

High dose Compound I (180 µmol/kg) is neuroprotective regarding striatonigral degeneration in MSA mice (FIG. 4). Evident on TH immunopositive cells in the substantia nigra, dopaminergic terminals in the striatum as well as the striatal DARPP-32 immunoreactive neurons.

Figure 5A:
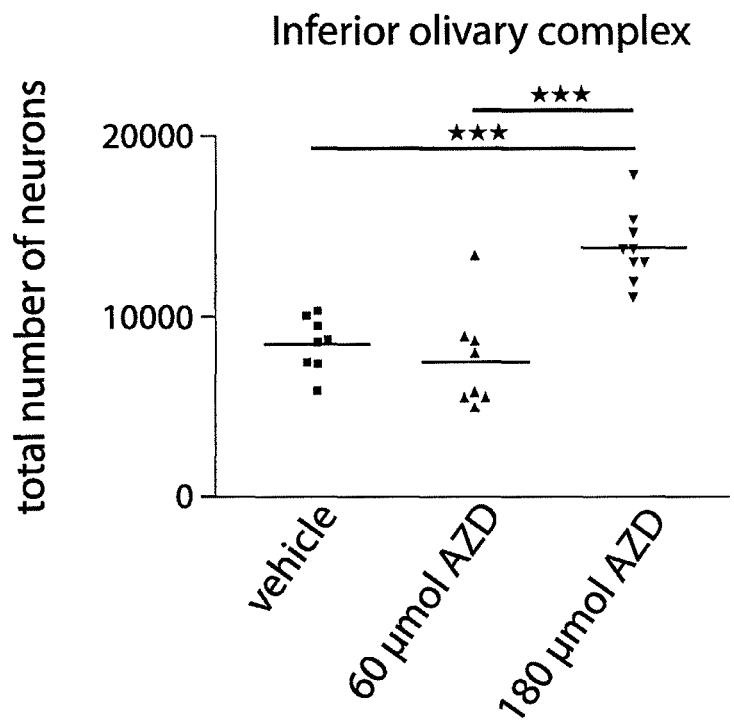
FIG. 5A is a graph depicting the total number of neurons in the inferior olivary complex in the cerebellum of MSA mice treated with AZD (compound I) and vehicle.
Figure 5B:
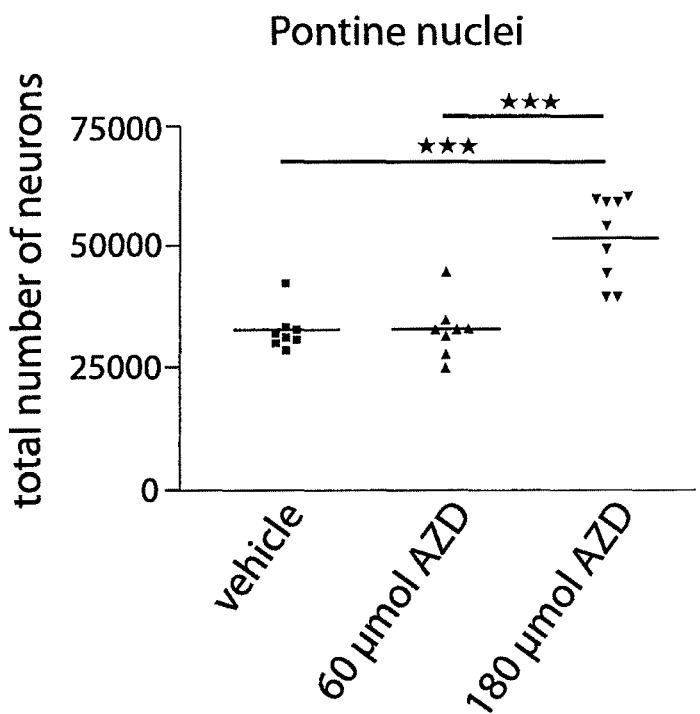
FIG. 5B is a graph depicting the total number of neurons in the pontine nuclei in the cerebellum of MSA mice treated with AZD (compound I) and vehicle.
Figure 5C:
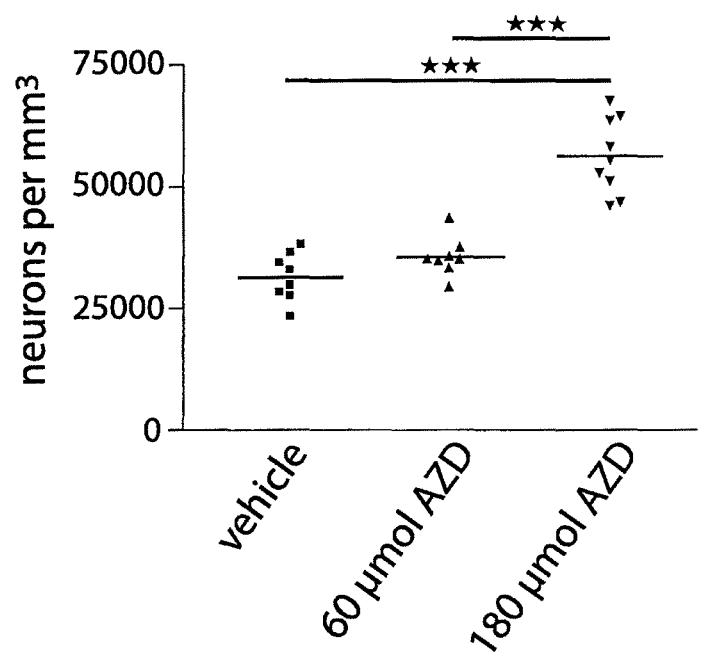
FIG. 5C is a graph depicting the neurons per $mm^3$ in the purkinje cells in the cerebellum of MSA mice treated with AZD (compound I) and vehicle.

High dose Compound I (180 µmol/kg) is neuroprotective regarding olivopontocerebellar atrophy in MSA mice. Protection of the inferior olivary complex, pontine nuclei and Purkinje cells in the cerebellum (FIG. 5).

Figure 6:
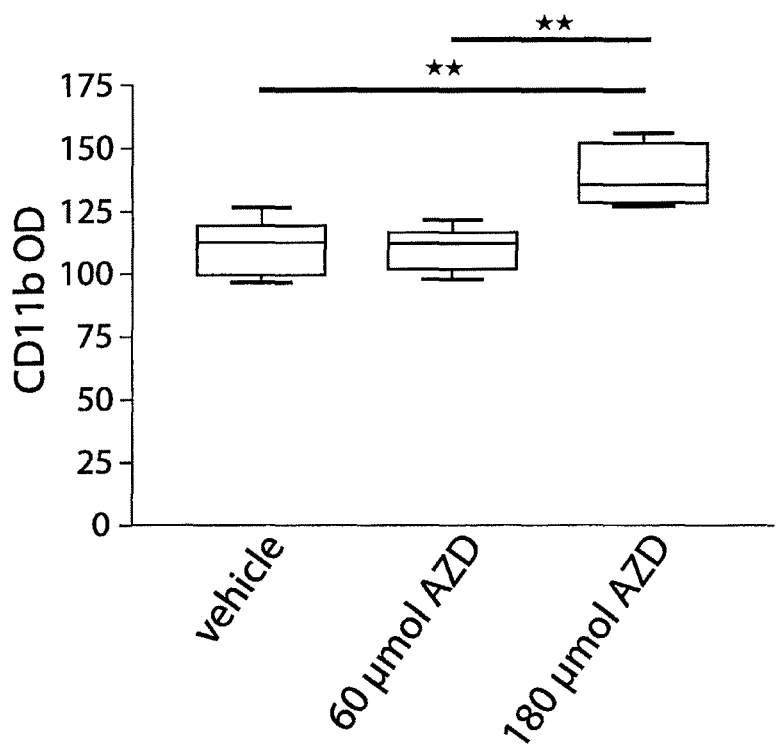
FIG. 6 is a graph depicting the microglial activation in the substantia nigra and striatum of MSA mice treated with AZD (compound I) and vehicle.
Figure 6:
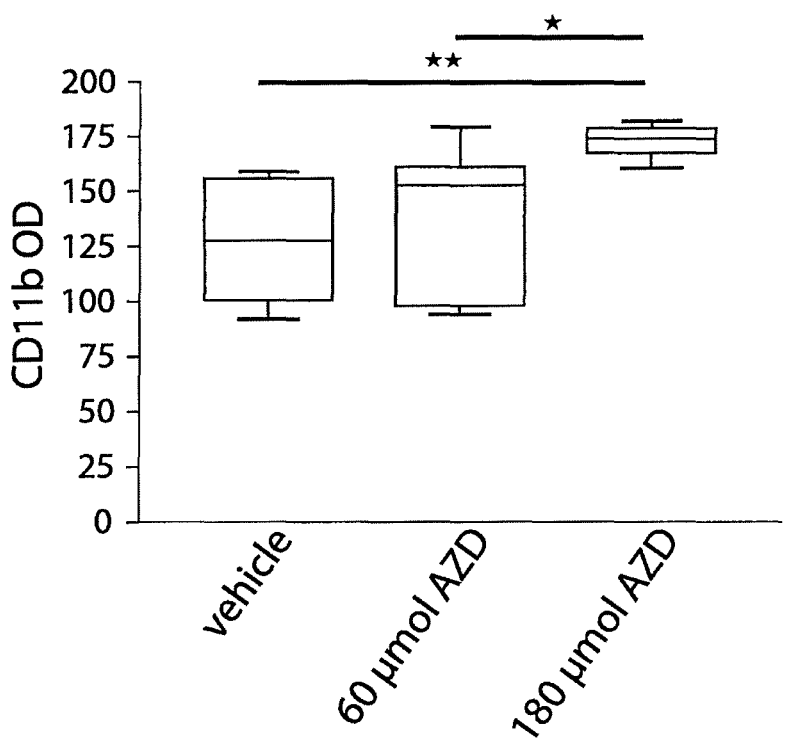

A high dose Compound I (180 µmol/kg) was associated with suppression of microglial activation, another marker of neuroinflammation, in MSA mice. This was seen both in the substantia nigra and the striatum (FIG. 6). This suggests that we have pharmacologically corroborated the previously suggested (Stefanova N. et al. Am. J. Pathol. 2005; 166: 869-76) link between microglia activation and neurodegeneration.

Summary of Findings

A significant neuroprotection was demonstrated with Compound I treatment. Neurons were consistently preserved at the level of substantia nigra pars compacta, striatum, cerebellar cortex, pontine nuclei, and inferior olivary complex. This neuroprotection was accompanied by a functional improvement measured by different behavioural tests. The Compound I effects were also related to suppression of microglial activation. The data supports that MPO inhibitors have a potential of being neuroprotective in conditions accompanied by neuroinflammation, including MSA, PD and HD.

A widespread neuroprotection, not limited to only a subset of neurons, through a reduced neuronal cell loss and/or reduced loss of neuronal terminals upon treatment in this kind of model with an MPO inhibitor will in addition support that MPO inhibitors have the potential to be neuroprotective also in human neurodegenerative disorders. A neuroprotection of all affected neuronal phenotypes, without any exception, in a model as described herein by MPO inhibitors should offer clear arguments for MPO inhibitors as being neuroprotective, not necessarily only limited to MSA, PD and Huntington's disease.

The invention claimed is:

1. A method for treating multiple system atrophy, comprising administering to a subject in need of such treatment an effective amount of 1-(2-isopropoxyethyl)-2-thioxo-1,2,3,5-tetrahydro-pyrrolo[3,2-d]pyrimidin-4-one or a pharmaceutically acceptable salt thereof.

2. The method according to claim 1, wherein the effective amount of 1-(2-isopropoxyethyl)-2-thioxo-1,2,3,5-tetrahydro-pyrrolo[3,2-d]pyrimidin-4-one or the pharmaceutically acceptable salt thereof is within the range of from 1 to 1000 mg.

* * * * *